United States Patent [19]

Haring et al.

[11] Patent Number: 5,911,986
[45] Date of Patent: Jun. 15, 1999

[54] FOODSTUFFS AND OTHER COMPOSITIONS

[75] Inventors: Petrus G. Haring, GV Vlaardingen; Petrus M. De Kok, BR Vlaardingen; Pieter De Geus, KB Barendrecht, all of Netherlands; Paul Davis, Felmersham, United Kingdom

[73] Assignee: Unilever Patent Holdings, B.V., Vlaardingen, Netherlands

[21] Appl. No.: 08/464,660

[22] PCT Filed: Dec. 21, 1993

[86] PCT No.: PCT/GB93/02610

§ 371 Date: Nov. 17, 1995

§ 102(e) Date: Nov. 17, 1995

[87] PCT Pub. No.: WO94/14934

PCT Pub. Date: Jul. 7, 1994

[30] Foreign Application Priority Data

Dec. 21, 1992 [GB] United Kingdom .................. 9226535

[51] Int. Cl.⁶ ................................................ A61K 39/395
[52] U.S. Cl. .................................... 424/130.1; 424/178.1; 530/300; 530/350; 530/387.1; 530/391.1; 530/389.1; 514/844
[58] Field of Search ...................... 530/300, 350, 530/387.1, 391.1; 424/389.1, 130.1, 178.1; 514/844

[56] References Cited

U.S. PATENT DOCUMENTS

| | | |
|---|---|---|
| 3,376,198 | 4/1968 | Petersen et al. . |
| 4,089,942 | 5/1978 | Bore et al. . |
| 4,610,877 | 9/1986 | Pearson et al. . |
| 5,030,722 | 7/1991 | Snyder et al. . |
| 5,057,424 | 10/1991 | Knuth et al. . |
| 5,260,270 | 11/1993 | Snyger et al. . |
| 5,573,922 | 11/1996 | Hoess et al. . |

FOREIGN PATENT DOCUMENTS

| | | |
|---|---|---|
| 0 127 712 | 12/1984 | European Pat. Off. . |
| 0 132 674 | 2/1985 | European Pat. Off. . |
| 0 307 376 | 3/1989 | European Pat. Off. . |
| 0 310 299 | 4/1989 | European Pat. Off. . |
| 0 335 654 | 4/1989 | European Pat. Off. . |
| 0 434 317 A1 | 6/1990 | European Pat. Off. . |
| 0 376 851 | 7/1990 | European Pat. Off. . |
| 0 566 368 A2 | 10/1993 | European Pat. Off. . |
| 1 424 304 | 2/1976 | United Kingdom . |
| 2 137 880 | 10/1984 | United Kingdom . |
| WO 90/01537 | 2/1990 | WIPO . |
| WO 90/15077 | 12/1990 | WIPO . |
| WO 91/08482 | 6/1991 | WIPO . |
| WO 91/11105 | 8/1991 | WIPO . |
| WO 91/11988 | 8/1991 | WIPO . |
| WO 92/12733 | 8/1992 | WIPO . |

OTHER PUBLICATIONS

Lee et al *Science* (1987) 235 (4792) pp. 1053–1056, Abstract only.
Bakalgar et al *Current Opinion in Neurobiology* (19910 vol. 1 pp. 204–208.
Abouzied et al *J. Agric Food Chem* (1990) vol. 38 pp. 331–335.
Bakalgar et al *Science* (1990) vol. 250 pp. 1403–1406.
Middlebrooks et al *Abstracts of the Annual Meeting of the American Society for Microbiology* (1987) p. 304.
Windholz et al (eds) " The Merck Indexs, Tenth Edition." Merck and Company, Inc. USA. pp. 34–35 1983.
Harlowe and Lane, "Antibodies, A Laboratory Manual"USA pp. 626–627 and 630, 1998.
Kuby, Immunology (1992) W.H. Freeman and Company, pp. 122–123, 1992.
Bergner, Deutsche Lebensmittel–Rundschau, vol. 70, pp. 349–351 (1974).
Furia et al, Fenaroli's Handbook of Flavor Ingredients, vol. 2, 2nd Ed. USA, CRC Press, p. 3 (1975).
Overbosch et al, Food Reviews International, vol. 7, No. 2, pp. 137–184 (1991).
Zeng et al. Journal of Chemical Ecology, vol. 17, No. 7, pp. 1469–1463 (1991).
Dufour et al, J. Agric. Food Chem., vol. 38, pp. 1691–1695 (1990).

*Primary Examiner*—Anthony C. Caputa
*Assistant Examiner*—Heather A. Bakalgar
*Attorney, Agent, or Firm*—Pillsbury Madison & Sutro, LLP

[57] ABSTRACT

The perceptibility of an undesirable odoriferous substance, for example a malodour or an off-flavour in a foodstuff, is reduced by means of a poplypeptide with binding affinity thereto, such as an antibody to the odoriferous substance or a fragment of such an antibody.

23 Claims, No Drawings

FOODSTUFFS AND OTHER COMPOSITIONS

This is a national stage entry of PCT/GB93/02610.

This invention is concerned with flavours and fragrances. It is of course very well known that the flavour of a foodstuff is at least in part attributable to materials which have some volatility and are perceived by the olfactory sense of the human body.

We have now appreciated that it is possible to make use of the binding affinity which is characteristic of binding proteins such as antibodies as a means of controlling the perceptibility of odoriferous materials which may be present, more specifically undesirable flavours or fragrances or constituents thereof.

According to a first aspect of this invention there is provided a method of reducing the perceptibility of an odoriferous substance which comprises bringing the substance or a precursor thereof into contact with a polypeptide having a binding affinity for the substance or its said precursor, with an affinity constant $K_a$, as determined in water at 20° C., of at least $10^6$ mol$^{-1}$ liter. The term odoriferous material refers here to flavours and to odours. The application of the invention which is particularly envisaged is reduction of the perceptibility of an odoriferous substance whose presence is undesirable, notably an off-flavour or a malodour.

In a second aspect, this invention provides a composition containing a polypeptide having a binding affinity for an odoriferous substance or precursor therefor, with an affinity constant $K_a$, as determined in water at 20° C., of at least $10^6$ mol$^{-1}$ liter.

The binding polypeptide in this invention may be a protein or a smaller polypeptide. It is envisaged that the binding polypeptide will, generally, be an antibody to the odoriferous substance or precursor or a fragment of such antibody. For commercial reasons it is preferred that the polypeptide should be as small as possible, and so might sometimes be referred to merely as a "peptide" provided it achieves the required blinding.

Reversible binding by a polypeptide entails ligand-receptor type interactions between the polypeptide and the material which is bound to it.

When a polypeptide binds to a substance, there is an equilibrium between bound and unbound substance, which can be represented by the chemical equation:

$$A + S \rightleftharpoons AS$$

where A represents unbound polypeptide, S represents unbound substance and AS represents the complex of polypeptide and substance bound together. The concentrations are related by:

$$\frac{[AS]}{[A][S]} = K_a$$

where $K_a$ is a constant, referred to as the affinity constant. In this invention the value of $K_a$ is $10^6$ mol$^{-1}$ liter or greater. It may well have a value of at least $10^7$ or even at least $10^8$ mol$^{-1}$ liter for example in the range $10^7$ to $10^9$ mol$^{-1}$ liter which is typical of the specific binding affinity between an antibody and an antigen.

It will be appreciated that with an affinity constant of $10^6$ mol$^{-1}$ liter or more, the value of [S], i.e. the equilibrium concentration of unbound substance, can be much less than it would be in the absence of the polypeptide, hence considerably reducing the perceptibility of the substance S.

Materials such as antibodies and fragments which bind with affinity constants of $10^6$ mol$^{-1}$ liter or greater will usually display such affinity rather specifically for a single substance or closely related substances. By reason of specificity for an undesirable substance or a precursor therefore, it is possible to reduce the perceptibility of that substance selectively, in the presence of other odoriferous substances whose presence is desirable and whose perceptibility is reduced to a relatively lesser extent if at all.

Thus there can be reduction in the perceptibility of an off-flavour, i.e. a flavour substance considered undesirable without suppression of desired flavour. Correspondingly, there can be reduction in malodour without suppression of a fragrance or odour which is desired.

In embodiments of this invention it may well be the case that the concentration of binding polypeptide and the affinity coefficient $K_a$ are both sufficiently high in relation to the concentration of the substance or precursor which is to be bound that at least 90% of this substance or precursor is bound to the polypeptide. This means that in a composition containing the polypeptide and the substance or precursor the ratio $$\frac{[AS]}{[AS] + [S]} = 0.9$$

Odoriferous substances generally have molecular weights not over 1000, indeed usually not over 500. Compounds of higher molecular weights do not normally produce a strong odour impact (which holds both for fragrances and the odour and part of a flavour).

The partial vapour pressure of the substance is related to the concentration of the unbound substance. Hence, when the invention is implemented by contacting an odoriferous substance with a protein or peptide having a specific binding affinity for that substance, binding of the protein or peptide to the odoriferous substance will reduce the partial vapour pressure of the substance and make the presence of the substance less apparent to the human sense of smell.

A precursor of an odoriferous substance is another substance which may or may not possess odour of its own and is converted to the odoriferous substance by a chemical change, possibilities for which include biochemical transformations and dissociation reactions.

When the invention is implemented by contacting the precursor of an odoriferous substance with a polypeptide, is having binding affinity for the precursor, the resulting complex of precursor and polypeptide may be hindered sterically and thereby prevented from undergoing transformation to the odoriferous substance. Alternatively, when that transformation can still occur the polypeptide may remain bound to the odoriferous substance thereby reducing the partial vapour pressure thereof.

As mentioned above the binding polypeptide may be an antibody but it is strongly preferred to utilise fragments of antibodies rather than whole antibodies. Fragments of antibodies can be produced using genetically modified bacteria, giving an economy in production compared with whole antibodies. Antibody fragments also provide more binding sites for the same weight of protein.

The invention may be utilised in a variety of ways. One utilisation which is specifically envisaged is as a means of suppressing the development of an off-flavour in a foodstuff. Certain foods incorporate precursor materials which undergo chemical change to produce impurities with a pungent off-flavour. By incorporating polypeptide with binding affinity to such an off-flavour impurity, traces of the impurity will be bound and its perceptibility will be reduced. By incorporating polypeptide with binding affinity to the precursor, its conversion to off-flavour may be inhibited, and/or the resulting off-flavour may be is bound, and its perceptibility reduced.

Thus in another aspect this invention provides a foodstuff including therein polypeptide with binding affinity to an off-flavour substance or precursor thereof liable to occur in the foodstuff, with an affinity constant $K_a$, as determined in water at 20° C., of at least $10^6$ mol$^{-1}$ liter.

Foodstuffs to which the invention may be applied include fatty and oily materials, for instance triglycerides, diglycerides and monoglycerides, also foods which have a substantial content of fatty or oily material, e.g. 25% by weight or more.

Another utilisation which is envisaged is as a way to reduce human body malodour. Existing cosmetic products for this purpose are generally antiperspirants which act against the secretion of sweat, or deodorants which act to prevent development of malodorous substances from ingredients of sweat. The latter often act by killing the bacteria on the skin surface to which they are applied.

In this aspect the invention provides a cosmetic product (i.e. composition) for application to human skin containing, in a cosmetically acceptable vehicle, polypeptide with binding affinity to a constituent of body malodour or precursor thereof, with an affinity constant $K_a$, as determined in water at 20° C., of at least $10^6$ mol$^{-1}$ liter.

The present invention requires polypeptide with binding affinity for an odoriferous substance or a precursor therefor. In order to obtain such a host animal may be immunised with the substance, or precursor, so as to raise polyclonal antibodies. Such procedures are well known.

Monoclonal antibodies may be obtained from these by standard techniques.

Antibody fragments which are used may be an Fab or Fv fragment, or the variable region of a heavy chain (a Dab fragment) or of a light chain. Some antibody fragments, notably Fab fragments, can be obtained by enzymic digestion of whole antibodies. Preferred routes to antibody fragments are through recombinant DNA technology, so that the fragment is expressed by a genetically transformed organism.

Antibody fragments produced by recombinant DNA technology need not be identical to fragments of antibodies produced in other ways. For instance they may include sequences of amino acids which differ from those found in antibodies produced in other ways, especially sequences at the ends of the fragments. Somewhat analogously, antibody fragments produced through recombinant DNA technology may include extra amino acid sequences at their termini which have no counterpart in antibodies produced in other ways.

Techniques for the production of antibody fragments are well known in the literature. Relevant disclosures include:
Saiki et al Science 230 1350–54 (1985);
Orlandi et al PNAS USA 86 3833–7 (1989);
WO 89/9825 (Celltech);
EP-A-368684 (Medical Research Council);
WO 91/8482 (Unilever).

A related possibility is that a binding agent for use in this invention is a synthetic polypeptide which mimics the specific binding activity of a natural antibody's complementarity determining region(s). Such a polypeptide is de facto a fragment of an artificial antibody.

The invention will be further described and illustrated by means of the following Examples.

EXAMPLE 1

An experiment was carried out using the synthetic perfumery material 6-acetyl-1-isopropyl-2,3,3,5-tetramethylindane which is available from Quest International, Naarden, The Netherlands under their trade mark Traseolide.

Monoclonal antibodies to Traseolide were obtained by conventional techniques.

The molecular weight of these antibodies was estimated as approximately 160,000 enabling the preparation of suspensions of known molarity.

A number of solutions were prepared and used in forced choice tests in which each member of a panel is offered a pair of solutions and asked to choose the solution with the more intense odour. In each case the panel consisted of thirty persons who had been selected as having ability to discriminate odours. The number of panellists picking each solution was recorded. In such a test if the number of panellists who choose one solution is much greater than the number who choose the other solution then the test demonstrates that the solutions are significantly different whereas if the numbers are approximately equal it indicates that the solutions are in fact indistinguishable and the choice of solution is random.

Selection of the same sample by 20 or more panellists is statistically significant at 95% confidence. Selection by 22 or more is significant at 99% confidence level.

All of the solutions were based on 20 mM phosphate buffer of pH 7.5. The various pairs of solutions and the number of panellists choosing each in a forced choice test are set out in the following Table. In some solutions gelatin was incorporated as a comparison. In one solution different monoclonal antibodies of an irrelevant specificity (antibodies to S. aureus) were incorporated as a comparison.

| Paired Comparison | Sample 1 | Chosen by | Sample 2 | Chosen by |
| --- | --- | --- | --- | --- |
| A | Buffer only | 6 | 0.1 μM Traseolide | 24 |
| B | Buffer only | 8 | 0.005 μM Traseolide | 22 |
| F | 0.1 μM Traseolide 0.1% gelatin | 12 | 0.1 μM Traseolide | 18 |
| D | 0.1 μM Traseolide anti-Traseolide | 5 | 0.1 μM Traseolide anti-X | 25 |

From the tests A and B in the Table above it can be seen that Traseolide can be detected in solution even at the low level of 0.005 μM. Test F shows that the incorporation of 0.1% by weight gelatin into 0.1 μM Traseolide solution does not make the solutions distinguishable to an extent which is statistically significant at a level of 95% confidence. Moreover, the perception of the difference between the gelatin-containing and gelatin-free solutions is less pronounced than the perception of 0.005 mM Traseolide.

By contrast test D demonstrates that the incorporation of antibodies to Traseolide renders the solution very perceptibly different from a comparative solution containing the same amount of Traseolide but with antibodies which do not bind to it.

This Example is a model for the reduction of the perceptibility of an odour which is undesirable.

EXAMPLE 2

An experiment was carried out demonstrating the ability of antibodies to reduce the perceptibility of vanillin (3-methoxy-4-hydroxybenzaldehyde).

Vanillic acid (3-methoxy-4-hydroxybenzoic acid) was conjugated to hens egg ovalbumin by means of carbodiimide. The product from this was emulsified with Freund's complete adjuvant and injected intramuscularly into a rabbit. Blood samples were taken from the rabbit before this immunisation and ten weeks after the immunisation. The serum was isolated from each of the blood samples.

The presence of polyclonal antibodies in the serum taken after immunisation was determined by the following assay. Vanillic acid was conjugated to hens egg ovalbumin with carbodiimide as before. The resulting conjugate was immobilised on solid phase nylon pegs pretreated with glutaraldehyde. Hens egg ovalbumin alone was immobilised on other nylon pegs. The pegs were incubated with the rabbit serum in various dilutions then washed and incubated with a commercial anti-rabbit alkaline phosphatase conjugate. The pegs were then washed again and placed in a solution of p-nitrophenyl phosphate at pH 9.8 where the alkaline phosphatase brings about a calorimetric reaction. The optical density was measured. This provides a measurement of the binding of rabbit antibodies to the pegs. The results are set out in the following Table.

|  | Optical Densities at 410 nm | |
|---|---|---|
|  | Pegs bearing Ovalbumin + vanillic acid | Pegs bearing Ovalbumin only |
| Serum dilution 1/100 | | |
| Pre-immunisation | 0.177 | 0.272 |
| Post-immunisation | 1.521 | 0.821 |
| Serum dilution 1/1000 | | |
| Pre-immunisation | 0.028 | 0.046 |
| Post-immunisation | 1.021 | 0.527 |
| Serum dilution 1/10,000 | | |
| Pre-immunisation | 0.009 | 0.018 |
| Post-immunisation | 0.443 | 0.115 |

The serum taken after immunisation shows much greater binding to ovalbumin demonstrating the development of antibodies to ovalbumin. The binding to ovalbumin-vanillic acid conjugate was greater still demonstrating that antibodies to vanillic acid have been obtained by immunisation.

This was confirmed by a competitive inhibition assay. Vanillic acid was again conjugated to ovalbumin using carbodiimide and the resulting conjugate was immobilised on nylon pegs. Serum taken after immunisation was mixed with vanillic acid at various concentrations. A control was mixed with diluent only. The resulting mixtures were incubated for sixty minutes at ambient temperature in wells of a microtitre plate. Then after this incubation the pegs bearing the ovalbumin-vanillic acid conjugate were inserted into the wells and incubated for thirty minutes.

The pegs were next removed, washed and inserted into wells containing anti-rabbit Ig conjugated to alkaline phosphatase and incubated for sixty minutes. The pegs were then removed, washed again and incubated with a reaction mixture in which any alkaline phosphatase which has become bound to the pegs causes development of colour. This was observed by determination of optical density. The results are set out in the following Table.

| Serum initially incubated with | Optical density at 410 nm |
|---|---|
| Diluent only (control) | 0.800 |
| 10 µg/ml vanillic acid | 0.682 |
| 100 µg/ml vanillic acid | 0.435 |

The results in the Table above confirm that there is less binding of antibodies to the pegs if the serum is previously incubated with vanillic acid at concentrations of 10 µg/ml or 100 µg/ml. This demonstrates the presence of antibodies to vanillic acid in the serum. In the case of the control, where the serum was not incubated with vanillic acid before insertion of the pegs, antibodies to ovalbumin and also antibodies to vanillic acid both bound to the pegs, and subsequently enabled the binding of acid phosphatase conjugate and the development of colour. By contrast when the serum was incubated with 10 µg/ml or 100 µg/ml vanillic acid, at least some of the antibodies bound to this with the result that these antibodies were not available to bind to the pegs and there was reduced development of colour.

The competitive assay was repeated, using vanillin in the initial incubation. Similar results were obtained, as set out in the following Table.

| Serum initially incubated with | Optical density at 410 nm |
|---|---|
| Diluent only (control) | 0.745 |
| 1 µg/ml vanillin | 0.592 |
| 10 µg/ml vanillin | 0.419 |
| 100 µg/ml vanillin | 0.266 |

These results show that the rabbit antibodies to vanillic acid bind also (and for that matter bind slightly better) to vanillin.

Ability to reduce the odour of Vanillin was demonstrated by means of a panel test. Each of four panellists was provided with a reference solution which was 10 µg/ml Vanillin in water. Each panellist confirmed that they could detect a distinct odour of vanilla.

Vials were prepared containing equal volumes of the above vanillin solution and rabbit serum. One of the vials contained serum taken after immunisation, the other vial contained serum taken before immunisation. These two vials were then presented to each of the panellists who was asked to score the vanilla odour on a five point scale running from zero=no vanilla odour to 4=same odour as reference solution.

The results were the same for each of the four panellists and were:

| Sample | Vanilla odour |
|---|---|
| 10 µg/ml vanillin (reference) | 4 |
| 10 µg/ml vanillin plus pre-immunisation serum | 3 |
| 10 µg/ml vanillin plus post-immunisation serum | 0–1 |

This experiment demonstrates that the presence of anti-vanillin antibodies serves to reduce the perceived vanilla odour. It also serves as a model for the reduction of an off-flavour.

EXAMPLE 3

This Example is a feasibility study for an envisaged application of the invention.

A known problem with triglycerides, i.e. fats and oils is the generation of off-flavours during storage. An instance of this arises with soya bean oil in which the development of an off-flavour is caused primarily by the presence of 3-methyl-2,4-nonadione. It has been shown that the threshold concentration at which this flavour component is perceptible is lower by a factor of 20 than for other substances capable of appearing as an off-flavour in soya bean oil. (Guth et al. Lebensm.-Wiss. u-Technology 23 513–522 (1990)).

A sample of 9-methyl-8,10-dioxo-undecanoic acid was synthesised chemically. The synthesis was in accordance with Pendarvis and Hampton J. Org. Chem 39 2290 (1974). This acid incorporates a structure similar to 3-methyl-2,4-nonadione.

This acid was conjugated by means of carbodiimide to an immunogenic protein (keyhole limpet haemocyanin).

Mice were immunised with the resulting conjugate by standard procedures. Serum was taken from the mice over a period of three months and found to contain polyclonal antibodies to 9-methyl-8,10-dioxo-undecanoic acid. It is intended that these polyclonal antibodies will be used to produce monoclonal antibodies to the acid and that these monoclonal antibodies will be effective as scavengers capable of binding 3-methyl-2,4-nonadione in stored soya bean oil.

If soya bean oil containing an amount $L^o$ of the 3-methyl-2,4-nonadione off-flavour is intimately mixed with an equal volume of water containing an amount E of unbound antibodies then the amounts of off-flavour in the oil ($L_{oil}$) and in the water ($L_w$) and the amount of off-flavour bound to antibody (EL) will be given by the relationships $$L^o = L_{oil} + L_w + EL$$

$$\frac{L_{oil}}{L_w} = K_e \quad \frac{EL}{L_w \times E} = K_a$$

where $K_e$ is the oil-water distribution coefficient and $K_a$ is the affinity constant for the complex of 3-methyl-2,4-nonadione and antibody thereto.

A predicted value for $K_a$, which is in line with affinity constants for good antibody-hapten complexes is $10^8$ mol$^{-1}$ liter. A likely value for $K_e$ is 1000. Using these predicted values it can be calculated that binding of 90% of the off-flavour substance in a realistic concentration range, thereby reducing its apparent concentration by a factor of 10 would require a concentration of the antibody of around 10 $\mu$M. Using antibody fragments rather than whole monoclonal antibodies would require a smaller concentration by weight of polypeptide to produce the same effect, which would be beneficial.

EXAMPLE 4

A savoury spread food product is prepared from a soya concentrate, vegetable oil, sodium chloride, water and minor amounts of herbs and spices to give a desired flavour.

To prevent the development of a soya-type off-flavour, without destroying the desired flavour, an antibody fragment with specific binding affinity for 3-methylnonane-2,4-dione are incorporated at a concentration of at least 25 mg protein per liter (which concentration corresponds to about 10 micromolar).

The antibody fragment was added to the food product as an agueous dispersion, with a corresponding reduction in the volume of water which was included.

EXAMPLE 5

This example concerns a cosmetic product for use as a deodorant. It has been reported in the literature that isovaleric acid is a significant constituent of human body malodour, e.g. Zeng et al J. Chemical Ecology 17 1469 (1991).

Isovaleric acid is conjugated to hens' egg ovalbumin and used to raise polyclonal antibodies in a manner directly analogous to Example 2.

Such antibodies are incorporated in a saline solution thickened with either a synthetic polymeric thickener, e.g. a cross-linked polyacrylate or a plant extract such as an alginate to provide a cosmetic composition. This is packed in roll-on applicators of the type conventionally used for underarm deodorants.

We claim:

1. A method of treating a foodstuff to reduce the perceptibility to a human of an undesirable odour or flavour of an odoriferous substance in said foodstuff which comprises contacting the substance or a precursor therefor which is convertible into said odoriferous substance by chemical change of said precursor, with an antibody or fragment thereof having binding specificity for the substance or precursor, with an affinity constant $K_a$, as determined in water at 20° C., of at least $10^6$ mol$^{-1}$ liter whereby said antibody or fragment thereof binds to said substance or precursor to thereby reduce the perceptibility of said undesirable odour or flavour of the foodstuff.

2. A method according to claim 1 wherein at least 90% by weight of the substance or precursor is bound by the antibody or fragment thereof.

3. A foodstuff including therein an antibody or fragment thereof having binding specificity for an odoriferous substance or a precursor thereof, which is convertible into said odoriferous substance by chemical change of said precursor, with an affinity constant $K_a$, as determined in water at 20° C., of at least $10^6$ mol$^{-1}$ liter whereby said antibody or fragment thereof binds to said substance or precursor therefor to thereby reduce odour otherwise caused by said substance.

4. A foodstuff according to claim 3 which is a fatty or oily material selected from the group consisting of triglycerides, diglycerides and monoglycerides.

5. A foodstuff according to claim 3 which contains at least 25% by weight of fat or oil.

6. A foodstuff according to claim 3, in which at least 90% by weight of the substance or precursor is bound by the antibody or fragment thereof.

7. A foodstuff according to claim 3 wherein the odoriferous substance is an unwanted flavour substance, the perceptibility of which is reduced relative to other flavour substances.

8. A cosmetically acceptable composition for application to human skin comprising a cosmetically acceptable vehicle containing an antibody or fragment thereof having binding specificity for a constituent of human body malodour or a precursor of such constituent, which is convertible into said odoriferous substance by chemical change of said precursor, with an affinity constant $K_a$, as determined in water at 20° C., of at least $10^6$ mol$^{-1}$ liter whereby said antibody or fragment thereof binds to said constituent or precursor therefor to reduce said malodour.

9. A foodstuff according to claim 5 in which at least 90% by weight of the substance or precursor is bound by the antibody or fragment thereof.

10. A foodstuff according to claim 5 wherein the odoriferous substance is an unwanted flavour substance, the perceptibility of which is reduced relative to other flavour substances.

11. A foodstuff according to claim 5 wherein the odoriferous substance is an unwanted flavour substance, the perceptibility of which is reduced relative to other flavour substances, and wherein at least 90% by weight of the said unwanted flavour substance is bound by the antibody or fragment thereof.

12. A method according to claim 1 wherein a fragment of an antibody to said odoriferous substance or said precursor of said substance, is used.

13. A method according to claim 1 wherein said odoriferous substance has a molecular weight not exceeding 1000.

14. A method according to claim 1 wherein said odoriferous substance is an off-flavour in a foodstuff.

15. A method according to claim 14 wherein said foodstuff contains at least 25 by weight of fat or oil.

16. A foodstuff according to claim 3 wherein said odoriferous substance has a molecular weight not exceeding 1000.

17. A cosmetically acceptable composition according to claim 8 wherein a fragment of an antibody to said odoriferous substance or precursor thereof is used.

18. A cosmetically acceptable composition according to claim 8 wherein said odoriferous substance has a molecular weight not exceeding 1000.

19. A cosmetically acceptable composition according to claim 8 wherein at least 90% by weight of the substance or precursor thereof is bound by the antibody or fragment thereof.

20. A method of reducing the human perceptibility of the undesired odour of an odoriferous substance or a precursor therefor which is convertible into said odoriferous substance by chemical change of said precursor, being a constituent of human body malodour, comprising applying a cosmetically acceptable composition to human skin, said cosmetically acceptable composition comprising an antibody or fragment thereof having binding specificity for the substance or precursor, with an affinity constant $K_a$, as determined in water at 20° C., of at least $10^6$ $mol^{-1}$ liter whereby said antibody or fragment thereof binds to said substance or precursor to thereby reduce said perceptibility of odour.

21. A method according to claim 20 wherein at least 90% by weight of the substance or precursor is bound by the antibody or fragment thereof.

22. A method according to claim 20 wherein a fragment of an antibody to said odoriferous substance or precursor thereof is used.

23. A method according to claim 20 wherein said odoriferous substance has a molecular weight not exceeding 1000.

* * * * *